United States Patent
Andrew et al.

(10) Patent No.: US 12,420,051 B2
(45) Date of Patent: Sep. 23, 2025

(54) METHODS AND SYSTEM FOR ANESTHETIC VAPORIZER DROP DETECTION

(71) Applicant: GE Precision Healthcare LLC, Waukesha, WI (US)

(72) Inventors: Charles Andrew, Greensboro, NC (US); Sandeep Punjalkatte Baliga, McFarland, WI (US); Karl N Knauf, Madison, WI (US); Russell J Kuzelka, McFarland, WI (US)

(73) Assignee: GE PRECISION HEALTHCARE LLC, Waukesha, WI (US)

(*) Notice: Subject to any disclaimer, the term of this patent is extended or adjusted under 35 U.S.C. 154(b) by 977 days.

(21) Appl. No.: 17/451,441

(22) Filed: Oct. 19, 2021

(65) Prior Publication Data
US 2023/0124901 A1   Apr. 20, 2023

(51) Int. Cl.
*A61M 16/18* (2006.01)
*A61M 16/00* (2006.01)
(Continued)

(52) U.S. Cl.
CPC .......... *A61M 16/18* (2013.01); *G16H 40/20* (2018.01); *G16H 40/67* (2018.01);
(Continued)

(58) Field of Classification Search
CPC .............. A61M 16/18; A61M 16/0087; A61M 16/186; A61M 2205/18; A61M 2205/3553; A61M 2205/581; A61M 2205/583; A61M 16/12; A61M 16/01; A61M 16/104; A61M 16/0078; A61M 16/1015; A61M 16/125; A61M 16/183; A61M 16/201;
(Continued)

(56) References Cited

U.S. PATENT DOCUMENTS 6,639,512 B1   10/2003   Lee et al.
7,704,227 B2   4/2010   Moberg et al.
(Continued)

FOREIGN PATENT DOCUMENTS

IE   S20120372 A2 * 11/2013 ............... A61B 5/00

OTHER PUBLICATIONS

"Human Factors Design Guide—Section 14 Contents," ERGO-EG Website, Available Online at http://www.ergo-eg.com/uploads/digi_lib/116.pdf, Jan. 15, 1996, 59 pages.
(Continued)

*Primary Examiner* — Kendra D Carter
*Assistant Examiner* — Arielle Wolff
(74) *Attorney, Agent, or Firm* — McCoy Russell LLP

(57) ABSTRACT

Systems and methods are provided for detecting unacceptable accelerations by an anesthetic vaporizer, such as due to drops and mishandling. In one embodiment, a method for an anesthetic vaporizer comprises determining a quantitative acceleration of the anesthetic vaporizer based on acceleration vectors measured by an accelerometer coupled within the anesthetic vaporizer, and outputting an alert responsive to the quantitative acceleration exceeding an acceleration threshold. In this way, drop-related degradation may be identified in a timely fashion.

19 Claims, 3 Drawing Sheets

(51) Int. Cl.
  *G01P 15/00* (2006.01)
  *G01P 15/18* (2013.01)
  *G16H 40/20* (2018.01)
  *G16H 40/67* (2018.01)

(52) U.S. Cl.
  CPC ....... *A61M 16/0087* (2013.01); *A61M 16/186* (2013.01); *A61M 2205/18* (2013.01); *A61M 2205/3553* (2013.01); *A61M 2205/581* (2013.01); *A61M 2205/583* (2013.01); *G01P 15/00* (2013.01); *G01P 15/18* (2013.01)

(58) Field of Classification Search
  CPC ................ A61M 16/208; A61M 16/22; A61M 2016/0027; A61M 2016/0039; A61M 2016/0042; A61M 2016/1035; A61M 2202/0208; A61M 2202/0266; A61M 2202/0283; A61M 2205/27; A61M 2205/3368; A61M 2205/3561; A61M 2205/3592; A61M 16/0051; A61M 16/024; A61M 2205/332; A61M 2205/3334; A61M 2205/502; A61M 2205/587; A61M 2205/8206; G16H 40/20; G16H 40/67
  See application file for complete search history.

(56) References Cited

U.S. PATENT DOCUMENTS

| | | |
|---|---|---|
| 8,217,795 B2 * | 7/2012 | Carlton-Foss ....... A61B 5/0024 340/4.1 |
| 8,665,097 B2 | 3/2014 | Worthington et al. |
| 10,699,811 B2 | 6/2020 | Gilham et al. |
| 2012/0101411 A1 * | 4/2012 | Hausdorff ............. A61B 5/1117 600/595 |
| 2012/0109575 A1 | 5/2012 | Balbus |
| 2022/0027823 A1 * | 1/2022 | Singh .................... G06Q 10/10 |
| 2022/0184309 A1 * | 6/2022 | Rosinko ................ G06F 1/3215 |

OTHER PUBLICATIONS

"Means to Discern Excessive Physical Shock to a Medical Vaporizer and Uses ED—Darl Kuhn", ip.com, ip.com Inc., West Henrietta, NY, US, Oct. 17, 2013 (Oct. 17, 2013), XP013159474, ISSN: 1533-0001.

EP application 22199842.0 filed Oct. 5, 2022—extended Search Report issued Mar. 17, 2023; 9 pages.

Haslam et al: "Principles of anaesthetic vaporizers", Mar. 1, 2004, vol. 5, No. 3, Mar. 1, 2004 (Mar. 1, 2004), pp. 88-91, XP005770277.

* cited by examiner

METHODS AND SYSTEM FOR ANESTHETIC VAPORIZER DROP DETECTION

FIELD

Embodiments of the subject matter disclosed herein relate to anesthesia systems, and more particularly, to systems and methods for monitoring an anesthetic vaporizer.

BACKGROUND

During some medical procedures, such as surgical procedures, a patient may be placed under general anesthesia by administrating an anesthetic agent. In some examples, the anesthetic agent may be a volatile anesthetic agent that is administered to the patient via an anesthetic vaporizer. For example, the anesthetic vaporizer may induce and control vaporization of the volatile anesthetic agent from a liquid form. A carrier gas (e.g., a mixture of oxygen and fresh air) may flow into the vaporizer and blend (e.g., mix and converge) with the anesthetic agent vapors before flowing to the patient, where they may be introduced via inhalation, for example, via a mask or breathing tube.

It may be desirable to ensure that the anesthetic vaporizer does not unintentionally emit anesthetic gases to the surrounding environment during operation and during storage. For example, anesthetic gases may escape from various coupling locations within the anesthetic vaporizer. Similarly, it may be desirable to ensure that the anesthetic vaporizer functions as intended so that a dosage of the anesthetic agent provided to the patient is controlled.

BRIEF DESCRIPTION

In one aspect, a method for an anesthetic vaporizer comprises determining a quantitative acceleration of the anesthetic vaporizer based on acceleration vectors measured by an accelerometer coupled within the anesthetic vaporizer, and outputting an alert responsive to the quantitative acceleration exceeding an acceleration threshold. In this way, drop-related degradation may be more easily identified, thus reducing usage of anesthetic vaporizers that may have degraded functionality.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The present disclosure will be better understood from reading the following description of non-limiting embodiments, with reference to the attached drawings, wherein below.

DETAILED DESCRIPTION

Figure 1:
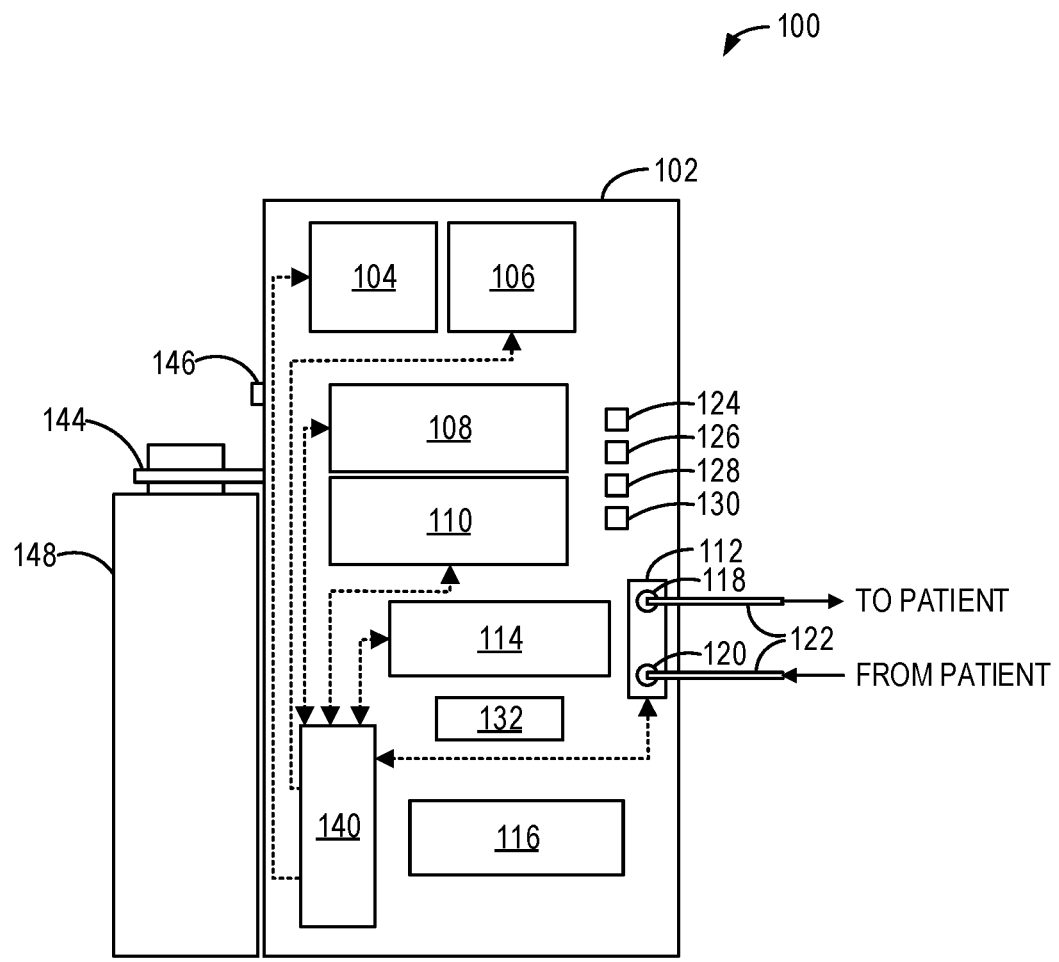
FIG. 1 schematically shows an embodiment of an anesthesia machine.

Embodiments of the present disclosure will now be described, by way of example, with reference to the FIGS. 1-3, which relate to various embodiments for detecting drop-related degradation of an anesthetic vaporizer. Anesthetic gases of an anesthetic agent may be intentionally generated for delivery to a patient using an anesthetic vaporizer included in an anesthesia machine. However, in some examples, the anesthetic vaporizer may become degraded due to mishandling, for example, or not being properly secured during transport. As a result, the anesthetic vaporizer may not be able to connect appropriately to the anesthesia machine and/or may not be able to deliver the anesthetic gases at an intended concentration. As another example, the degradation may result in the anesthetic vaporizer emitting the anesthetic agent while the anesthetic vaporizer is not in use, such as when the anesthetic vaporizer is unpowered.

Currently available anesthetic vaporizers do not have the capability to actively monitor for degradation that may be caused by drops or falls of the anesthetic vaporizer. As a result, healthcare professionals using or storing the anesthesia machine may not be alerted to leaks or other functional issues. Because the anesthetic gases may diffuse into the environment surrounding the anesthesia machine, healthcare professionals may be unintentionally exposed to the anesthetic agent. Overall, the anesthetic gases may decrease air quality in the environment surrounding the anesthesia machine. Further, the patient may not receive an intended dose of the anesthetic gases.

Thus, embodiments described herein include a method and system for alerting an operator of the anesthetic vaporizer to detected drops and impacts of the anesthetic vaporizer that may result in degradation of the anesthetic vaporizer. For example, the system may include an accelerometer that records acceleration vectors even while the anesthetic vaporizer is unpowered. While the anesthetic vaporizer is powered, a controller may receive the recorded acceleration vectors and trigger an alert (e.g., alarm) if the anesthetic vaporizer has experienced unacceptable acceleration that may result in degradation of the anesthetic vaporizer.

The embodiments disclosed herein may provide several advantages. For example, the alert may enable medical personnel to identify and isolate potentially degraded equipment, allowing the medical personnel to proactively manage air quality in the clinical environment as well as effectively provide anesthetic gases to a patient. As an example, the alarming anesthetic vaporizer may not be used until it is evaluated for degradation by a qualified technician. Further, by actively monitoring a direction of the acceleration, anesthetic vaporizer repair may be expedited. Further still, by actively monitoring for drops that may result in anesthetic vaporizer degradation, unwanted vapors may be removed from the clinical environment, increasing air quality. Overall, by providing an active alerting system, the medical personnel may have increased confidence that a non-alarming anesthetic vaporizer has not undergone an unacceptable fall.

FIG. 1 schematically shows an embodiment of an anesthesia machine. FIG. 2 shows an embodiment of an anesthetic vaporizer that may be included in the anesthesia machine of FIG. 1. In particular, the anesthetic vaporizer includes a battery-operated accelerometer that records acceleration vectors even while the anesthetic vaporizer is powered off. FIG. 3 shows an exemplary method for identifying unacceptable drops and rough handling of the anesthetic vaporizer of FIG. 2 based on the acceleration vectors recorded by the accelerometer and outputting an alarm in response. Thus, methods and systems are provided for reducing unidentified drop-related anesthetic vaporizer degradation, thereby reducing inadvertent healthcare professional exposure to anesthetic gases and increasing patient anesthetic dosage accuracy.

Turning now to the figures, FIG. 1 schematically shows an example anesthesia machine 100. The anesthesia machine 100 includes a frame (or housing) 102. In some embodiments, the frame 102 may be supported by casters, where the movement of the casters may be controlled (e.g., stopped) by one or more locks. In some examples, the frame 102 may be formed of a plastic material (e.g., polypropylene). In other examples, the frame 102 may be formed of a different type of material (e.g., metal, such as steel).

The anesthesia machine 100 also includes an anesthesia display device 104, a patient monitoring display device 106, a respiratory gas module 108, one or more patient monitoring modules, such as a patient monitoring module 110, a ventilator 112 (explained in more detail below), an anesthetic vaporizer 114, and an anesthetic agent storage bay 116. The anesthesia machine 100 may further include a main power indicator 124, a system activation switch 126 (which, in one example, permits gas flow when activated), an oxygen flush button 128, and an oxygen control 130. An example embodiment of the anesthetic vaporizer 114 will be described below with respect to FIG. 2. The anesthetic vaporizer 114 may vaporize the anesthetic agent and combine the vaporized anesthetic agent with one or more medical grade gases (e.g., oxygen, air, nitrous oxide, or combinations thereof), which may then be delivered to a patient.

The anesthesia machine 100 may additionally include an integrated suction, an auxiliary oxygen flow control, and various other components for providing and/or controlling a flow of the one or more medical grade gases to the patient. In the embodiment shown, the anesthesia machine 100 includes one or more pipeline connections 146 to facilitate coupling of the anesthesia machine to pipeline gas sources. Additionally, the anesthesia machine 100 includes a cylinder yoke 144, via which one or more gas-holding cylinders 148 may be coupled to the anesthesia machine. Thus, through the pipeline connection and/or cylinder connections, gas may be provided to the anesthesia machine, where the gas may include (but is not limited to) medical air, oxygen, nitrogen, and nitrous oxide. The gas that enters the anesthesia machine may mix with the vaporized anesthetic agent at the anesthetic vaporizer 114, as described above, before being supplied to a patient via ventilator 112. The anesthesia machine may also include a serial port, a collection bottle connection, and a cylinder wrench storage area. Further, in some embodiments, the anesthesia machine may include an anesthesia gas scavenging system 132.

The ventilator 112 may include an expiratory check valve at an expiratory port 120, an expiratory flow sensor at the expiratory port 120, an inspiratory check valve at an inspiratory port 118, an inspiratory flow sensor at the inspiratory port 118, an absorber canister, a manual bag port, a ventilator release, an adjustable pressure-limiting valve, a bag/vent switch, and a bellows assembly. When a patient breathing circuit is coupled to the ventilator 112, breathing gases (e.g., air, oxygen, and/or nitrous oxide mixed with vaporized anesthetic agent) exit the anesthesia machine from the inspiratory port 118 and travel to the patient. Expiratory gases from the patient re-enter the anesthesia machine via expiratory port 120, where carbon dioxide may be removed from the expiratory gases via absorber canister.

During operation of the anesthetic vaporizer 114, an operator (e.g., an anesthesiologist) may adjust an amount of vaporized anesthetic agent that is supplied to the patient by adjusting a flow rate of gases from the gas source(s) (e.g., the pipeline gas supply) to the vaporizer. The flow rate of the gases from the gas source to the vaporizer may be adjusted by the operator via one or more flow adjustment devices. For example, the flow adjustment devices may include analog and/or digital adjustment dials and/or other user input devices configured to actuate one or more flow control valves of the anesthesia machine 100. In some embodiments, a first flow control valve may be positioned between the gas source(s) and the anesthetic vaporizer 114 and may be actuatable via flow adjustment devices to a fully open position, a fully closed position, and a plurality of positions between the fully open position and the fully closed position.

The anesthesia machine 100 may additionally include one or more valves configured to bypass gases from the gas source(s) around the anesthetic vaporizer 114. The valves may enable a first portion of gases to flow directly from the gas source to the inspiratory port 118 and a second portion of gases to flow from the gas source through the anesthetic vaporizer 114 to mix with the vaporized anesthetic agents prior to flowing to the inspiratory port 118. By adjusting a ratio of the first portion of gases relative to the second portion of gases, the operator may control a concentration of vaporized anesthetic agent administered to the patient via inspiratory port 118.

Further, the adjustments described above may be facilitated at least in part based on output from the respiratory gas module 108. The respiratory gas module 108 may be configured to measure various parameters of the gases exiting the vaporizer and/or being provided to the patient. For example, the respiratory gas module 108 may measure the concentrations of carbon dioxide, nitrous oxide, and the anesthetic agent provided to the patient. Further, the respiratory gas module 108 may measure respiration rate, minimum alveolar concentration, patient oxygen, and/or other parameters. The output from the respiratory gas module 108 may be displayed via a graphical user interface on a display device (e.g., the anesthesia display device 104 and/or the patient monitoring display device 106) and/or used by a controller to provide closed-loop feedback control of the amount of anesthesia provided to the patient.

The ventilator 112 may optionally be coupled to a breathing circuit (not shown) including a plurality of tubes (e.g., gas passages) 122. The breathing circuit may be coupled between an airway of a patient (e.g., via a breathing mask positioned to enclose the mouth and/or nose of the patient or a tracheal intubation tube) and the inspiratory port 118. Gases (e.g., the one or more medical gases, or a mixture of the one or more medical gases and vaporized anesthetic agent from the anesthetic vaporizer 114) may flow from the inspiratory port 118, through the breathing circuit, and into the airway of the patient, where the gases are absorbed by the lungs of the patient. By adjusting the concentration of vaporized anesthetic agent in the gases as described above, the operator may adjust a degree to which the patient is anesthetized.

During conditions in which the breathing circuit is coupled to the airway, the anesthetic agent and/or fresh gas (without the anesthetic agent) may flow into the airway of the patient (e.g., through inhalation) via inspiratory port 118 and the inspiratory check valve. As an example, the inspiratory check valve may open automatically (e.g., without input or adjustment by the operator) in response to inhalation by the patient and may close automatically in response to exhalation by the patient. Similarly, the expiratory check valve may open automatically in response to exhalation by the patient and may close automatically in response to inhalation by the patient.

In some embodiments, the operator may additionally or alternatively control one or more operating parameters of the anesthesia machine 100 via an electronic controller 140 of the anesthesia machine 100. The controller 140 includes a processor operatively connected to a memory. The memory may be a non-transitory computer-readable medium and may be configured to store computer executable code (e.g., instructions) to be processed by the processor in order to execute one or more routines, such as those described herein. The memory may also be configured to store data received by the processor. The controller 140 may be communicatively coupled (e.g., via wired or wireless connections) to one or more external or remote computing devices, such as a hospital computing system, and may be configured to send and receive various information, such as electronic medical record information, procedure information, and so forth. The controller 140 may also be electronically coupled to various other components of the anesthesia machine 100, such as the anesthetic vaporizer 114, the ventilator 112, the respiratory gas module 108, the anesthesia display device 104, and the patient monitoring display device 106.

The controller 140 receives signals from the various sensors of the anesthesia machine 100 and employs the various actuators of the anesthesia machine 100 to adjust operation of the anesthesia machine 100 based on the received signals and instructions stored on the memory of the controller. For example, the flow of gases to the inspiratory port 118 may be controlled via an input device (e.g., keyboard, touchscreen, etc.) coupled to the electronic controller of the anesthesia machine 100. The controller 140 may display operating parameters of the anesthesia machine 100 via anesthesia display device 104 and/or the patient monitoring display device 106. The controller may receive signals (e.g., electrical signals) via input device and may adjust operating parameters of the anesthesia machine 100 in response (e.g., responsive) to the received signals.

As one example, the operator may input a desired concentration of the anesthetic agent to be delivered to the patient. A corresponding valve position of one or more valves of the anesthesia machine (e.g., a position of one or more bypass valves, as described above) may be empirically determined and stored in a predetermined lookup table or function in a memory of the controller. For example, the controller may receive the desired concentration of the anesthetic agent via input device and may determine an amount of opening of the one or more valves corresponding to the desired concentration of the anesthetic agent based on the lookup table, with the input being the concentration of the anesthetic agent and the output being the valve position of the one or more valves. The controller may transmit an electrical signal to an actuator of the one or more valves in order to adjust each of the one or more valves to the corresponding output valve position. In some examples, the controller may compare the desired flow rate of gases to a measured flow rate of gases, such as measured by the inspiratory flow sensor, for example.

The controller 140 is shown in FIG. 1 for illustrative purposes, and it is to be understood that controller 140 may be located in various locations within, around, and/or remote from the anesthesia machine 100. As an example, the controller 140 may include multiple devices/modules that may be distributed throughout the anesthesia machine 100. As such, the controller 140 may include a plurality of controllers at various locations within the anesthesia machine 100. As another example, additionally or alternatively, the controller 140 may include one or more devices/modules that are external to the anesthesia machine 100, located proximate to (e.g., in a same room) or remote (e.g., at a remote server) from the anesthesia machine 100. In each example, the multiple devices/modules may be communicatively coupled through wired and/or wireless connections.

Anesthetic vaporizers, such as the anesthetic vaporizer 114 shown in FIG. 1, may employ various methods to vaporize a liquid anesthetic agent. For example, the anesthetic vaporizer 114 may use a flow-over method (in which a carrier gas flows over a top surface of a volatile liquid anesthetic agent), a bubble-through method (in which the carrier gas is bubbled up through the liquid anesthetic agent), or a gas/vapor blender (in which heat is used to vaporize the liquid anesthetic agent, and the vapors are injected into a fresh gas flow). Regardless of the vaporization method, in some embodiments, the anesthetic vaporizer 114 may include a sump for storing the liquid anesthetic agent before it is delivered to a vaporizing chamber.

Figure 2:
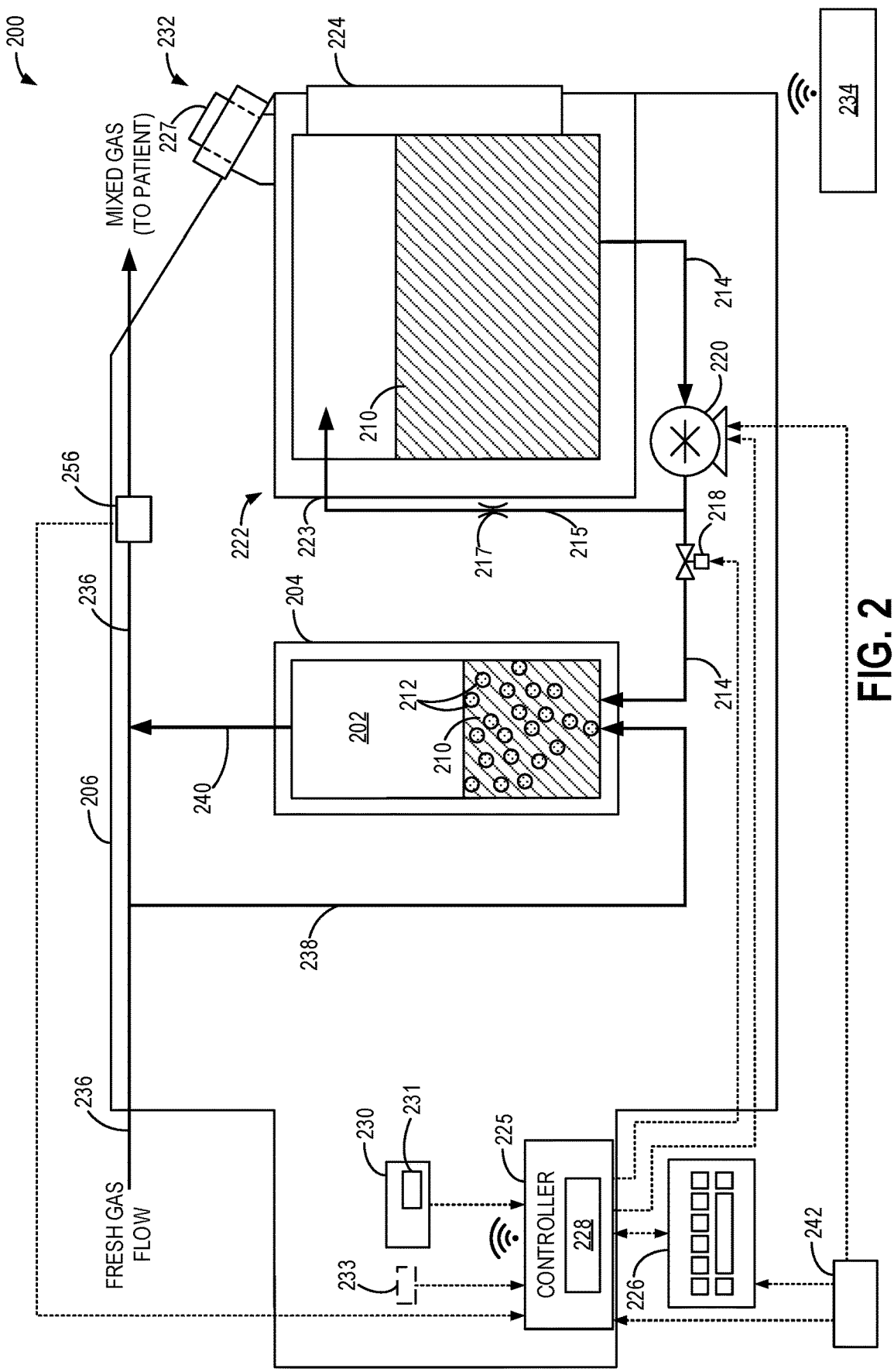
FIG. 2 schematically shows an embodiment of an anesthetic vaporizer that may be included in an anesthesia machine.

FIG. 2 shows an exemplary embodiment of an anesthetic vaporizer 200, which may be included in an anesthesia machine (e.g., the anesthesia machine 100 shown in FIG. 1). As one example, the anesthetic vaporizer 200 may be the anesthetic vaporizer 114 of FIG. 1. In the embodiment shown in FIG. 2, the anesthetic vaporizer 200 is a bubble-through anesthetic vaporizer, including a vaporizing chamber 202 defined by a housing 204. However, in other embodiments, the anesthetic vaporizer 200 may be another type of anesthetic vaporizer (e.g., flow-over, injector-based, wick-based, etc.) for use with a volatile liquid anesthetic agent, and the bubble-through architecture is shown for illustrative purposes.

A lower portion of the vaporizing chamber 202 is shown holding a liquid anesthetic agent 210 that is supplied from a sump 222 via a conduit 214 and a pump 220. The liquid anesthetic agent 210 may be isoflurane, sevoflurane, or another liquid anesthetic agent of similar volatility, for example, that is stored in the sump 222. The pump 220 may be a positive displacement pump, such as a reciprocating positive displacement pump, for example. The pump 220 may be selectively operated to deliver the liquid anesthetic agent 210 from the sump 222 to the vaporizing chamber 202 in response to a command signal from a controller 225, as will be further described below. The controller 225 may be an electronic controller including a processor operatively connected to a memory 228, which may be a non-transitory (e.g., read-only) memory that stores instructions executable by the processor. The controller 225 may be included in (e.g., a part of) or communicatively coupled to the controller 140 shown in FIG. 1, for example.

The sump 222 is defined by a housing 223. The housing 223 and the housing 204 may be integrated with or positioned with an external housing 206 of the anesthetic vaporizer 200. For example, the pump 220, the conduit 214, etc. may be internal components within the external housing 206. The sump 222 may be refilled via a filler apparatus 232 positioned on an exterior of the housing 223 and the housing 206. The filler apparatus 232 includes a filler port 227. In some embodiments, the filler apparatus 232 may further include a fill cap (not shown in FIG. 2) configured to cover the filler port 227 when a refilling event is not occurring. For example, an operator of the anesthetic vaporizer 200 may remove the fill cap to refill the sump 222 with additional liquid anesthetic agent 210 (e.g., from a refill bottle) via the filler port 227 and then replace the fill cap to seal the sump 222. The fill cap may be a screw cap, for example. Thus, in some embodiments, the sump 222 may be a sealed system when the fill cap is in place. In some embodiments, a sight glass 224 may enable the operator to evaluate a fill status of the sump 222.

The conduit 214 may further include a shut-off valve 218 coupled between the pump 220 and the vaporizing chamber 202. For example, the shut-off valve 218 may be an on-off valve, wherein the shut-off valve 218 is actuated to an open (e.g., fully open) position that allows the liquid anesthetic agent 210 to flow between and the pump 220 and the vaporizing chamber 202 or a closed (e.g., fully closed) position that prevents (e.g., blocks) the flow of the liquid anesthetic agent 210 between the pump 220 and the vaporizing chamber 202. The shut-off valve 218 may be actuated between the open and closed positions in response to a command signal from the controller 225, for example. A liquid return line 215 may be coupled to the conduit 214 between the shut-off valve 218 and the pump 220 to reduce a pressure build-up between the shut-off valve 218 and the pump 220, such as when the shut-off valve 218 is closed. For example, an excess amount of the liquid anesthetic agent 210 provided by the pump 220 may be returned to the sump 222 via the liquid return line 215. Further, the liquid return line 215 may include a restriction 217, such as an orifice, to control flow through the liquid return line 215 such that the liquid anesthetic agent 210 preferentially flows through the shut-off valve 218 instead of the restriction 217 when the shut-off valve 218 is open.

The controller 225 may selectively activate the pump 220 to provide the liquid anesthetic agent 210 from the sump 222 to the vaporizing chamber 202. In one embodiment, the controller 225 may adjust operation of the pump 220 responsive to a measurement received from a level sensor coupled to the vaporizing chamber 202. As one example, the controller 225 may be configured to maintain the level of liquid anesthetic agent at a target level or within a target range in order to prevent both underfilling and overfilling of the vaporizing chamber 202.

In some embodiments, the pump 220 may include a positive displacement stepper motor, where each positive displacement step of the pump is equivalent to a specified volume of the liquid anesthetic agent 210. In this manner, the pump may be used to precisely fill the vaporizing chamber 202 and prevent overfilling by recording the number of pump steps delivered. This approach may also be used to record a volume of anesthetic agent delivered to the vaporizing chamber 202, which may be used for vaporizer run-time/maintenance analysis (e.g., service metrics), liquid leak detection, precise determination of an amount of liquid anesthetic remaining and available for delivery, vaporization efficiency calculations, etc.

An upper portion of the vaporizing chamber 202 (e.g., above a surface of the liquid anesthetic agent 210) holds vapor, which may be a mixture of vaporized anesthetic agent and a carrier gas from a fresh gas flow. The fresh gas flow, and thus the carrier gas, may include one or more medical grade gases, such as oxygen, air, nitrous oxide, and combinations thereof. The fresh gas flow may be provided via one or more gas pipelines (e.g., via the pipeline connections 146 shown in FIG. 1) and/or one or more gas-holding cylinders (e.g., the gas-holding cylinder 148 of FIG. 1). As shown in FIG. 2, the fresh gas flow may enter anesthetic vaporizer 200 via a first gas passage 236.

In the exemplary embodiment of FIG. 2, a second gas passage 238 branches off from first gas passage to provide carrier gas to the vaporizing chamber 202. As used herein, "carrier gas" refers to a portion of the fresh gas flow that flows to the vaporizing chamber 202, whereas "bypass gas" refers to a remaining portion of the fresh gas flow that does not flow through the vaporizing chamber 202, as will be elaborated below. For example, the second gas passage 238 may pass through an opening in the housing 204, which may include a gas-tight seal, to flow the carrier gas through a bottom of the vaporizing chamber 202. However, in other embodiments, the anesthetic vaporizer 200 may not include the second gas passage 238, and the carrier gas may not be delivered to the vaporizing chamber 202. For example, the carrier gas may not be delivered to the vaporizing chamber 202 when the liquid anesthetic agent 210 has a relatively low boiling point (e.g., at or around room temperature), such as when the liquid anesthetic agent 210 is desflurane or another liquid anesthetic agent of similar volatility. Additionally or alternatively, the second gas passage 238 may not be included in embodiments where a different type of anesthetic vaporizer architecture is used (e.g., a flow over type or a gas/vapor blender). Thus, the embodiment shown in FIG. 2 is provided by way of example.

The carrier gas delivered to the vaporizing chamber 202 via the second gas passage 238 flows through the liquid anesthetic agent 210 to form a plurality of gas bubbles 212. The plurality of gas bubbles 212 pass through the liquid anesthetic agent 210, becoming saturated with vaporized anesthetic agent, as they rise to the surface of the liquid. In some examples, a heating element may be coupled to or within the vaporizing chamber 202 to increase a temperature of the liquid anesthetic agent 210 and provide energy for vaporization (e.g., latent heat of vaporization).

Vapor, such as the carrier gas that is saturated with vaporized anesthetic agent, may flow out of the vaporizing chamber 202 via a third gas passage 240 (e.g., a vapor delivery passage). For example, the third gas passage 240 may pass through an opening at or near a top of the housing 204 and form a junction with the first gas passage 236 to fluidically couple the upper portion of the vaporizing chamber 202 with the first gas passage 236. Upstream of the junction with the third gas passage 240 and downstream of the junction with the second gas passage 238, the first gas passage 236 carries the bypass gas portion of the fresh gas flow. The bypass gas does not pass through the vaporizing chamber 202. The bypass gas, containing no vaporized anesthetic agent, and the vapor from the vaporizing chamber 202, containing the carrier gas saturated with the vaporized anesthetic agent, mix at and downstream of the junction between the first gas passage 236 and the third gas passage 240. The mixed gas may then be delivered to the patient via an inspiratory limb of a breathing circuit (e.g., via the inspiratory port 118 described with respect to FIG. 1).

In some embodiments, a concentration sensor 256 may be coupled to first gas passage 236 downstream of the junction with third gas passage 240. The concentration sensor 256 may be any suitable sensor that is configured to measure a concentration of the anesthetic agent in the mixed gas. As one example, the concentration sensor 256 may be an optical sensor that transmits light of a suitable wavelength (e.g., infrared) through the mixed gas and determines a concentration of the anesthetic agent based on an absorption of the light by the mixed gas. In other examples, the concentration sensor may be a carbon dioxide or oxygen sensor that measures the concentration of the anesthetic agent based on a displacement of the carbon dioxide or oxygen relative to a supplied concentration of carbon dioxide or oxygen in the fresh gas flow. The concentration sensor 256 may output a signal to the controller 225 indicative of the measured concentration of the anesthetic agent (e.g., the concentration of the anesthetic agent vapor) in the mixed gas.

The anesthetic vaporizer 200 further includes an accelerometer 230 coupled within the external housing 206. The accelerometer 230 may comprise a three-axis accelerometer, which may provide information about the orientation and motion of the anesthetic vaporizer 200. The accelerometer 230 may be rigidly affixed to a surface within the anesthetic vaporizer 200 (e.g., within the external housing 206) so that the accelerometer 230 does not move independently from the anesthetic vaporizer 200 as a whole. The accelerometer 230 may be used to calculate an orientation of the anesthetic vaporizer 200 as well as acceleration. For example, the three axes of the accelerometer 230 may generate an acceleration vector that will be resolved within the controller 225 to determine a quantitative acceleration that the anesthetic vaporizer 200 experienced as well as the direction of the acceleration, as will be elaborated below with respect to FIG. 3.

The accelerometer 230 includes a power source 231. The power source 231 may be a battery, such as a coin battery. The power source 231 provides continuous electrical power to the accelerometer 230 independently from the other components of the anesthetic vaporizer 200. That is, the power source 231 only powers the accelerometer 230, and thus the accelerometer 230 remains powered on and active even while the remaining components of the anesthetic vaporizer 200, including the controller 225, are powered off. For example, the controller 225, the pump 220, and other electronic components of the anesthetic vaporizer 200 receive electrical power from a system power source 242, which is distinct from and not electrically coupled to the power source 231, when the anesthetic vaporizer 200 is powered on. For example, at least a portion of the system power source 242 may be exterior to the external housing 206. When the anesthetic vaporizer 200 is not powered on, the anesthetic vaporizer 200 may be powered off and may not be receiving electrical power from the system power source 242. The system power source 242 may be a battery (e.g., a rechargeable battery), an electrical grid (e.g., accessed via a plug), a solar power grid, etc. The controller 225 may receive acceleration vectors that were recorded by the accelerometer 230 while the controller 225 was powered off upon power up (e.g., in response to a start-up operation of the anesthetic vaporizer 200), for example.

In addition to receiving signals output by the concentration sensor 256 and the accelerometer 230, the controller 225 may receive additional signals, including signals from one or more additional sensors 233 coupled in various locations throughout the anesthetic vaporizer 200. The one or more additional sensors 233 may comprise pressure, temperature, and volatile organic compound (VOC) sensors. Additionally or alternatively, the one or more additional sensors 233 may comprise a gyroscope, a level sensor, a touch sensor, and an ultrasonic leak sensor. For example, the gyroscope may measure an angular velocity of the anesthetic vaporizer 200, which may be used by the controller 225 in combination with data from the accelerometer 230 to determine tilt. Combining information from the gyroscope with information from the accelerometer 230 may result in a more accurate quantification of tilt, for example. As another example, in addition to using the level sensor to determine agent levels in the sump 222 during use, the level sensor may be activated in response to an acceleration measured by the accelerometer 230 exceeding a drop threshold in order to monitor the agent level in the sump 222 after the drop has occurred. Doing so may help identify if the drop caused degradation to components holding the liquid anesthetic agent 210. Identifying the drop based on the output of the accelerometer 230 will be further described below with respect to FIG. 3. As still another example, the touch sensor may be positioned on the external housing 206 and may be used to identify if and where the anesthetic vaporizer 200 was being held prior to the drop. For example, the touch sensor may detect that the anesthetic vaporizer 200 is being held on two opposing faces when the drop occurs, suggesting that a user was carrying the anesthetic vaporizer 200 when it was dropped. As yet another example, the ultrasonic leak detector may be used to listen for ultrasonic leaks within the anesthetic vaporizer 200 following a detected drop. For example, in response to the acceleration measured by the accelerometer 230 exceeding the drop threshold, the anesthetic vaporizer 200 may be pressurized (e.g., via a blower), and the ultrasonic leak detector may be activated to listen for leakage of the pressurized air from the anesthetic vaporizer 200. Doing so may help identify if degradation of the anesthetic vaporizer 200 has occurred during the drop.

The controller 225 receives the signals from the various sensors of FIG. 2, processes the input data, and employs the various actuators of FIG. 2 to adjust operation of anesthetic vaporizer 200 based on the received signals and instructions stored on a memory of the controller. Additionally, the controller 225 may output an alert to the operator via a human-machine interface (HMI) 226 that is operationally connected to the controller (e.g., via wired or wireless communication) responsive to detecting an unacceptable drop or fall. Further, data may be input to the controller 225 by the operator of anesthetic vaporizer 200 via the HMI 226. Thus, the HMI 226 may include both a user input device and an output device. The user input device may include one or more of a mouse, a keyboard, a voice input device, a touch input device for receiving a gesture from the operator, a motion input device for detecting non-touch gestures and other motions by the operator, and other comparable input devices, as well as associated processing elements capable of receiving user input from the operator. The output device may include one or more of a display (e.g., the anesthesia display device 104 and/or the patient monitoring display device 106 of FIG. 1) for providing visual alerts or text-based messages and a speaker for providing audible alerts or messages.

The controller 225 may further communicate with an inventory management system 234 that is external to the anesthetic vaporizer 200. For example, the inventory management system 234 may be remote from the anesthetic vaporizer 200, such as in a different location within a hospital. The inventory management system 234 may track a maintenance status, usage statistics, etc. of the anesthetic vaporizer 200 as well as other medical equipment within a medical facility. As one example, the controller 225 may communicate with the inventory management system 234 via wireless communication, such as via WiFi, Bluetooth, or near-field communication (NFC) protocols. For example, the controller 225 may transmit information regarding unacceptable drop detections to the inventory management system 234, as will be elaborated below with respect to FIG. 3.

The conduit 214, the shut-off valve 218, the pump 220, the first gas passage 236, the second gas passage 238, the third gas passage 240, and the liquid return line 215 may all include seal sites that may potentially become degraded during drops or mishandling. For example, the conduit 214, the shut-off valve 218, the pump 220, and the liquid return line 215 may be included in a pneumatic coupling system between the sump 222 and the vaporizing chamber 202. As an example, degradation of the seal sites may result in unintended emission of the anesthetic agent into the surrounding environment. As another example, degradation may result in decreased functionality of the anesthetic vaporizer. As still another example, the sight glass 224 may shatter or crack. As such, it may be desired to preemptively identify events such as falls and drops that may result in the degradation of the anesthetic vaporizer 200 so that timely inspection and any repairs may be performed before the vaporizer is attempted to be used for patient care.

Figure 3:
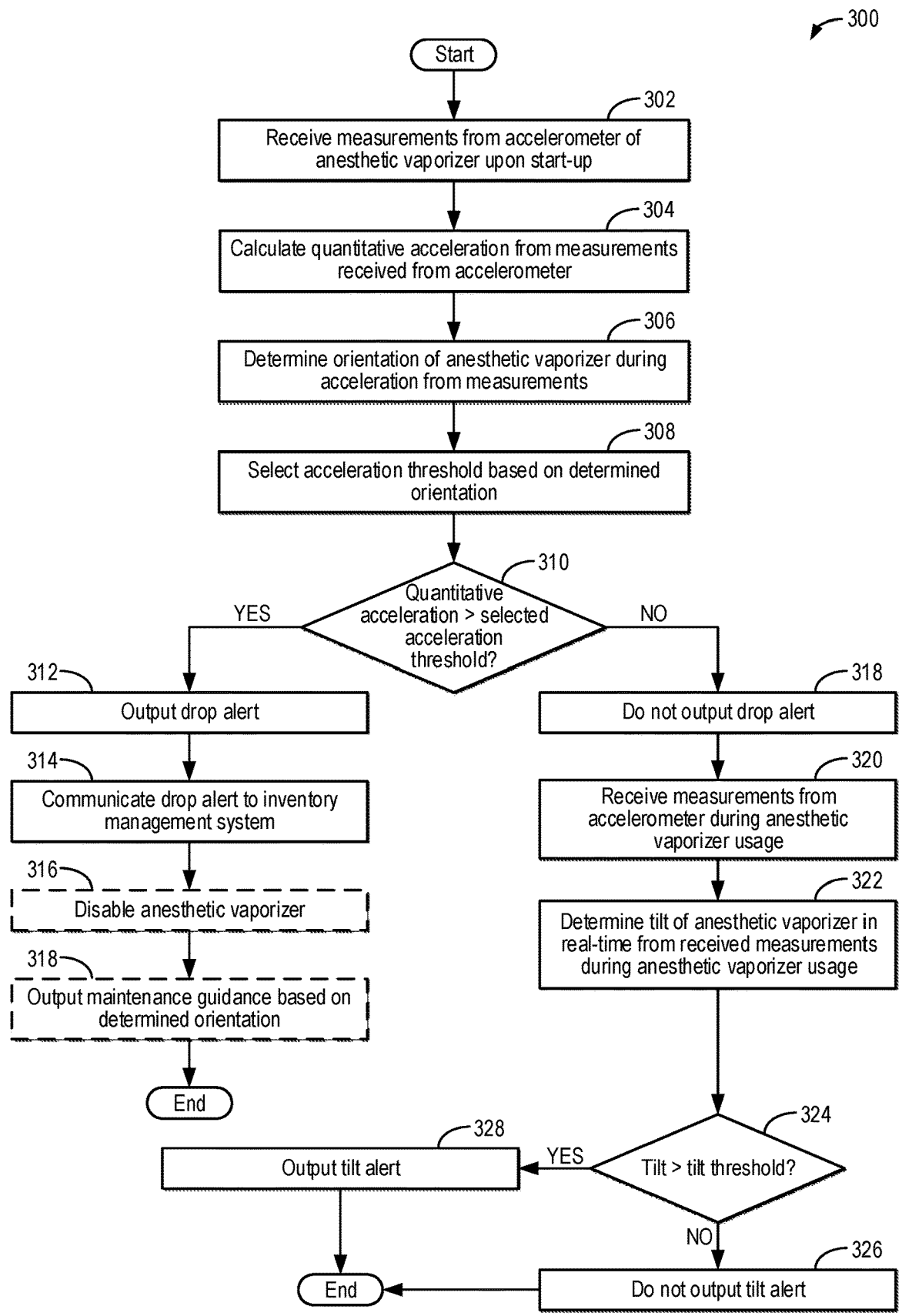
FIG. 3 a flow chart illustrating an exemplary method for detecting drop-related degradation of an anesthetic vaporizer.

Thus, FIG. 3 shows a flow chart of an example method 300 for detecting unacceptable acceleration and impact of an anesthetic vaporizer of an anesthesia machine. The anesthetic vaporizer may be the anesthetic vaporizer 200 of FIG. 2, for example. The method 300 and the rest of the methods included herein may be executed by a controller, such as the controller 225 of FIG. 2, according to instructions stored in a memory of the controller (e.g., the memory 228 of FIG. 2) and in conjunction with one or more inputs, such as inputs received from one or more sensors (e.g., the accelerometer 230 of FIG. 2). Further, the controller may output information to an operator of the anesthesia machine via a human-machine interface (e.g., the HMI 226 of FIG. 2).

At 302, the method 300 includes receiving measurements from the accelerometer of the anesthetic vaporizer upon start-up. As described above with respect to FIG. 2, the accelerometer may be a three-axis accelerometer that includes a separate power source from the anesthetic vaporizer. Thus, the accelerometer may record measurements in each of the three axes while the anesthetic vaporizer is powered down and then send the recorded measurements to the controller during a starting operation of the anesthetic vaporizer (e.g., in response to the anesthetic vaporizer being powered on from an unpowered state).

At 304, the method 300 includes calculating a quantitative acceleration from the measurements received from the accelerometer. For example, the acceleration measurements from the three axes may be resolved into an acceleration vector that has a magnitude and a direction. As one example, the controller may resolve the quantitative acceleration using a root sum squared method. That is, the three-axis accelerometer may acquire acceleration measurements in each axis (x, y, z) of three-dimensional space, and the resulting quantitative acceleration may be calculated by inputting the three acceleration measurements into a root sum squared equation:

$$\text{Resolved vector} = \sqrt{(x^2 + y^2 + z^2)},$$

where x is the x-axis acceleration, y is the y-axis acceleration, and z is the z-axis acceleration. As an illustrative example, the measured x-axis acceleration may be 1 milligravities (mG), the measured y-axis acceleration may be 15 mG, and the measured z-axis acceleration may be 50 mG, resulting in a resolved vector magnitude of 52.2 mG.

The angle of each measurement from the origin of the accelerometer axes may be determined by:

$$\cos(\text{angle}) = (\text{axis measurement}/\text{resolved vector}),$$

where axis measurement is the measured acceleration for a single axis (x, y, or z) and resolved vector is determined using the root sum squared equation, as shown above. Continuing the illustrative example, the x-axis angle would be 88.9 degrees, the y-axis angle would be 73.3 degrees, and the z-axis angle would be 16.7. The three angles enable the overall direction of the resolved acceleration vector to be defined in three-dimensional space.

At 306, the method 300 includes determining an orientation of the anesthetic vaporizer during the acceleration from the measurements. For example, the direction of the resolved acceleration vector may be used to determine the orientation of the anesthetic vaporizer during the acceleration. For example, the origin of the accelerometer may be associated with a known orientation of the anesthetic vaporizer. Further, the controller may have pre-programmed knowledge of the direction of each axis of the accelerometer with respect to the faces of the anesthetic vaporizer. As such, the controller may infer which face (e.g., side, top, or bottom) of the anesthetic vaporizer may have impacted with another surface, such as the ground.

At 308, the method 300 includes selecting an acceleration threshold based on the determined orientation. For example, some surfaces of the anesthetic vaporizer may become more easily degraded than others, such as where a sight glass is positioned. As another example, fragile internal components (or those more easily degraded) may be positioned more toward one surface of the anesthetic vaporizer relative to others. As such, the acceleration threshold may vary based on the determined orientation. As one example, the controller may select from a plurality of acceleration thresholds stored in memory, with each of the plurality of acceleration thresholds corresponding to a different direction of the acceleration (and thus, a different surface and orientation of the anesthetic vaporizer that undergoes impact). For example, the plurality of acceleration thresholds may be stored as an array or matrix, and the controller may input the determined orientation (or direction of the acceleration vector) into the array or matrix, which may output the corresponding acceleration threshold to use. As another example, the controller may adjust the acceleration threshold by a pre-determined amount based on the determined orientation, such as by increasing the acceleration threshold for orientations that are less prone to degradation and/or decreasing the acceleration threshold for orientations that are more prone to degradation.

Each acceleration threshold corresponds to a pre-determined acceleration value (e.g., in g-force) above which drop-related degradation is expected. For example, each acceleration value may further correspond to a threshold drop height above which evaluation for impact-related degradation is recommended before the anesthetic vaporizer is used for patient care. As discussed above, the threshold drop height may vary for each possible orientation of the anesthetic vaporizer at impact.

At 310, the method 300 includes determining if the quantitative acceleration is greater than the selected acceleration threshold. For example, the controller may directly compare the quantitative acceleration (e.g., the magnitude of the resolved acceleration vector, as determined at 304) to the selected acceleration threshold (e.g., as selected at 308) to determine if the quantitative acceleration is greater than the selected acceleration threshold.

In response to the quantitative acceleration being greater than the selected acceleration threshold, the method 300 proceeds to 312 and includes outputting a drop alert. The drop alert may be output by the HMI, for example, as an audible and/or visual alert (or alarm). For example, the audible alert may include an alarm sound that is output via speakers of the HMI. Additionally or alternatively, the audible alert may include a spoken message regarding the detected drop, including the quantitative (e.g., total) acceleration experienced and the determined orientation off the anesthetic vaporizer during the acceleration. In some examples, the drop alert may further include information regarding each individually measured acceleration vector comprising the quantitative acceleration, a number of the individually measured acceleration vectors comprising the quantitative acceleration, etc. For example, multiple smaller accelerations may result in a same quantitative acceleration as a single larger acceleration, and an amount of degradation expected may be different for the multiple smaller accelerations relative to the single larger acceleration. Similarly, the visual alert may include a drop alert symbol output via a display screen of the HMI, flashing lights, and/or a text-based message. For example, the text-based message may include information regarding the detected drop, including the determined orientation off the anesthetic vaporizer during the acceleration.

At 314, the method 300 includes communicating the drop alert to an inventory management system, which may be the inventory management system 234 of FIG. 2, for example. For example, the controller may communicate the drop alert to the inventory management system via WiFi, NFC, or another wired or wireless communication protocol. The inventory management system may track drop statistics, a maintenance status, a usage status, etc. of the anesthetic vaporizer as well as settings of the anesthetic vaporizer during use.

At 316, the method 300 optionally includes disabling the anesthetic vaporizer. For example, the controller may prevent the anesthetic vaporizer from being operated so that the anesthetic vaporizer may not be used until maintenance or inspection is performed and logged with the controller. As such, a likelihood that a degraded anesthetic vaporizer is used for patient care may be reduced. As a result, unintentional emission of the anesthetic agent to the environment may be reduced, and an accuracy of anesthetic agent delivery to a patient may be increased. However, in other embodiments of the method 300, 316 may be omitted, and a user may instead voluntarily choose to not use the anesthetic vaporizer based on the drop alarm.

At 318, the method 300 optionally includes outputting maintenance guidance based on the determined orientation. For example, the controller may communicate the maintenance guidance to the operator via the HMI and may further output the maintenance guidance to the inventory management system. In some embodiments, the maintenance guidance may include an audible message. In other embodiments, the maintenance guidance may additionally or alternatively include a visual message. The message may include information regarding particular components that are the most likely to be degraded due to the orientation of the anesthetic vaporizer at impact. For example, the maintenance guidance may include an inspection checklist so that the anesthetic vaporizer may be more efficiently inspected and/or repaired, thus reducing a down-time of the anesthetic vaporizer. As one example, the inspection checklist may be selected from a plurality of pre-determined inspection checklists based on the determined orientation of the anesthetic vaporizer at impact. However, in other embodiments of the method 300, 318 may be omitted.

The method 300 may then end. For example, the method 300 may be repeated at every start-up of the anesthetic vaporizer and at a pre-determined frequency while the anesthetic vaporizer is powered "on" in order to continue checking for drops and mishandling of the anesthetic vaporizer.

Returning to 310, in response to the quantitative acceleration not being greater than the selected acceleration threshold (e.g., the quantitative acceleration is less than or equal to the selected acceleration threshold), the method 300 proceeds to 318 and includes not outputting the drop alert. For example, even if non-zero acceleration was experienced, it is not expected to degrade the anesthetic vaporizer because it is less than the selected acceleration threshold. As such, the operator may not be alerted.

At 320, the method 300 includes receiving measurements from the accelerometer during anesthetic vaporizer usage. As such, the accelerometer may record data not only while the anesthetic vaporizer is powered down, but while the anesthetic vaporizer is in use. The accelerometer may transmit the measurements to the controller in real-time while the anesthetic vaporizer is powered on. As used herein, the term "real-time" may refer to simultaneous or substantially simultaneous detection and processing. As another example, the term "real-time" may refer to a process executed without intentional delay.

At 322, the method 300 includes determining a tilt of the anesthetic vaporizer in real-time from the received real-time measurements during the anesthetic vaporizer usage. For example, the measurements received from the accelerometer may be used to determine a real-time orientation of the anesthetic vaporizer, which may be used to determine the real-time tilt. In embodiments where a gyroscope is included in the anesthetic vaporizer, the controller may also receive real-time measurements of angular velocity from the gyroscope and determine the real-time tilt based on both of the real-time orientation determined from the accelerometer measurements and the angular velocity. The tilt of the anesthetic vaporizer may be an angle of the anesthetic vaporizer relative to a desired position defined as 0° of tilt. For example, the desired position may be an orientation where a bottom surface of the anesthetic vaporizer is parallel to (e.g., level with) a ground surface and closer to the ground surface than a top surface of the anesthetic vaporizer. As an example, the anesthetic vaporizer may become tilted during use during patient transport.

At 324, the method 300 includes determining if the tilt is greater than a tilt threshold. The tilt threshold may be a non-zero value stored in the memory of the controller above which the anesthetic vaporizer may not function as intended. As a non-limiting example, the tilt threshold may be 10° from the desired position. However, in other examples, the tilt threshold may be less than or greater than 10° from the desired position.

If the tilt is not greater than the tilt threshold, the method 300 proceeds to 326 and includes not outputting a tilt alert. As such, even if the anesthetic vaporizer is moved or jostled, the operator will not be alerted because the movement is not expected to affect anesthetic vaporizer function. The method 300 may then end.

Returning to 324, in response to the tilt being greater than the tilt threshold, the method 300 proceeds to 328 and includes outputting a tilt alert. The tilt alert may be output by the HMI, for example, as an audible and/or visual alert. For example, the audible alert may include an alarm sound that is output via speakers of the HMI. Additionally or alternatively, the audible alert may include a spoken message regarding the detected tilt, including a direction or degree of the tilt. Similarly, the visual alert may include a tilt alert symbol output via the display screen of the HMI, flashing lights, and/or a text-based message. For example, the text-based message may include the information regarding the detected tilt mentioned above. Further, the tilt alert may be a second type of alert that is different than the drop alert, which may be a first type of alert. The tilt alert may be further communicated to the inventory management system. The method 300 may then end.

Thus, the methods and systems described herein provide for detecting unacceptable drops, falls, and mishandling of an anesthetic vaporizer. As a result, an air quality in the environment surrounding the anesthetic vaporizer, such as in a surgical suite or other medical facility, may be increased. Further, inadvertent exposure of medical professionals to anesthetic gases may be decreased, and silent leaks within the anesthetic vaporizer may be determined, enabling maintenance of the anesthetic vaporizer to be prompted. Further still, an accuracy of anesthetic agent delivery to a patient may be increased by alerting operators to potential fall-related degradation as well as when the anesthetic vaporizer becomes tilted during use. Additionally, servicing of the anesthetic vaporizer may be expedited, resulting in reduced down-time of the anesthetic vaporizer.

A technical effect of measuring acceleration vectors of an anesthetic vaporizer and outputting an alert in response to a quantitative acceleration exceeding a threshold is that an operator may be alerted to impact-related degradation of the anesthetic vaporizer that may be otherwise unnoticed.

The disclosure also provides support for a method for an anesthetic vaporizer, comprising: determining a quantitative acceleration of the anesthetic vaporizer based on acceleration vectors measured by an accelerometer coupled within the anesthetic vaporizer, and outputting an alert responsive to the quantitative acceleration exceeding an acceleration threshold. In a first example of the method, the method further comprises: determining an orientation of the anesthetic vaporizer during the quantitative acceleration based on the acceleration vectors, and wherein the acceleration threshold is selected from a plurality of acceleration thresholds based on the determined orientation. In a second example of the method, optionally including the first example, each of the plurality of acceleration thresholds corresponds to a threshold drop height for each possible orientation of the anesthetic vaporizer. In a third example of the method, optionally including one or both of the first and second examples, the method further comprises: outputting maintenance guidance based on the determined orientation in response to the quantitative acceleration exceeding the acceleration threshold. In a fourth example of the method, optionally including one or more or each of the first through third examples, the alert includes information regarding the determined orientation and the quantitative acceleration. In a fifth example of the method, optionally including one or more or each of the first through fourth examples, the accelerometer is powered by a separate power source from the anesthetic vaporizer, and wherein determining the quantitative acceleration of the anesthetic vaporizer based on the acceleration vectors measured by the accelerometer coupled within the anesthetic vaporizer is responsive to the anesthetic vaporizer being powered on. In a sixth example of the method, optionally including one or more or each of the first through fifth examples, the acceleration vectors measured by the accelerometer coupled within the anesthetic vaporizer are measured while the anesthetic vaporizer is unpowered, and wherein the alert includes one or both of an audible alert and a visual alert. In a seventh example of the method, optionally including one or more or each of the first through sixth examples, the method further comprises: disabling usage of the anesthetic vaporizer in response to the quantitative acceleration exceeding the acceleration threshold and communicating the alert to an inventory management system. In an eighth example of the method, optionally including one or more or each of the first through seventh examples, the method further comprises: communicating the alert and a magnitude of each of the acceleration vectors to an inventory management system via a wireless communication protocol in response to the quantitative acceleration exceeding the acceleration threshold. In a ninth example of the method, optionally including one or more or each of the first through eighth examples, the method further comprises: determining a tilt of the anesthetic vaporizer during usage based on measurements received in real-time from the accelerometer coupled within the accelerometer, and outputting a tilt alert in response to the tilt of the anesthetic vaporizer exceeding a threshold tilt.

The disclosure also provides support for a system for an anesthetic vaporizer, comprising: an accelerometer positioned within an external housing of the anesthetic vaporizer, and a controller storing executable instructions in non-transitory memory that, when executed, cause the controller to: receive measurements from the accelerometer recorded while the anesthetic vaporizer is powered off, resolve a quantitative acceleration from the received measurements, determine an orientation of the anesthetic vaporizer from the received measurements, and output a first type of alert in response to the quantitative acceleration exceeding an acceleration threshold. In a first example of the system, the controller includes further instructions stored in the non-transitory memory that, when executed, cause the controller to: select the acceleration threshold from a plurality of different acceleration thresholds stored in the non-transitory memory based on the determined orientation. In a second example of the system, optionally including the first example, the system further comprises: a first power source that provides continuous electrical power to the accelerometer and a second power source that provides electrical power to the controller while the anesthetic vaporizer is powered on and not while the anesthetic vaporizer is powered off. In a third example of the system, optionally including one or both of the first and second examples, the controller includes further instructions stored in the non-transitory memory that, when executed, cause the controller to: receive real-time measurements from the accelerometer while the anesthetic vaporizer is powered on, determine a real-time tilt of the anesthetic vaporizer based on the real-time measurements received from the accelerometer, and output a second type of alert in response to the real-time tilt exceeding a tilt threshold.

The disclosure also provides support for a method for detecting a fall of an anesthetic vaporizer, comprising: upon start-up of the anesthetic vaporizer, receiving acceleration measurements recorded by an accelerometer coupled within the anesthetic vaporizer while the anesthetic vaporizer is powered off, determining a magnitude and direction of an acceleration vector from the acceleration measurements, selecting an acceleration threshold based on the direction of the acceleration vector, and outputting a drop alert in response to the magnitude of the acceleration vector exceeding the acceleration threshold. In a first example of the method, selecting the acceleration threshold based on the direction of the acceleration vector comprises inputting the direction of the acceleration vector into an array storing a plurality of acceleration thresholds, each of the plurality of acceleration thresholds corresponding to a different direction of the acceleration vector. In a second example of the method, optionally including the first example, the drop alert comprises an audible alarm. In a third example of the method, optionally including one or both of the first and second examples, the method further comprises: disabling the anesthetic vaporizer in response to the magnitude of the acceleration vector exceeding the acceleration threshold, and not disabling the anesthetic vaporizer in response to the magnitude of the acceleration vector not exceeding the acceleration threshold. In a fourth example of the method, optionally including one or more or each of the first through third examples, the method further comprises: outputting an inspection checklist in response to the magnitude of the acceleration vector exceeding the acceleration threshold. In a fifth example of the method, optionally including one or more or each of the first through fourth examples, the inspection checklist is selected from a plurality of different inspection checklists based on the direction of the acceleration vector, and wherein both of the drop alert and the inspection checklist are communicated to an inventory management system via wireless communication.

As used herein, an element or step recited in the singular and preceded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

This written description uses examples to disclose the invention, including the best mode, and also to enable a person of ordinary skill in the relevant art to practice the invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The invention claimed is:

1. A method for an anesthetic vaporizer, comprising:
measuring acceleration vectors with an accelerometer coupled within the anesthetic vaporizer, wherein the accelerometer is powered by a first power source that provides continuous electrical power to the accelerometer, and wherein the anesthetic vaporizer is powered by a second power source that provides electrical power while the anesthetic vaporizer is powered on and not while the anesthetic vaporizer is powered off;
determining a quantitative acceleration of the anesthetic vaporizer and an orientation of the anesthetic vaporizer during the quantitative acceleration based on the acceleration vectors measured by the accelerometer;
adjusting, via a controller, an acceleration threshold based on the orientation of the anesthetic vaporizer, wherein adjusting the acceleration threshold comprises increasing the acceleration threshold by a first predetermined amount responsive to a first orientation of the anesthetic vaporizer, and decreasing the acceleration threshold by a second predetermined amount responsive to a second orientation of the anesthetic vaporizer;
activating a sensor responsive to the quantitative acceleration exceeding the acceleration threshold; and
outputting an alert responsive to the quantitative acceleration exceeding the acceleration threshold.

2. The method of claim 1, wherein, in the second orientation, a first surface of the anesthetic vaporizer comprising a sight glass is positioned to face a direction of impact.

3. The method of claim 1, wherein the sensor is an ultrasonic leak detector, and wherein the ultrasonic leak detector measures leakage from the anesthetic vaporizer.

4. The method of claim 1, further comprising outputting maintenance guidance based on the determined orientation in response to the quantitative acceleration exceeding the acceleration threshold.

5. The method of claim 1, wherein the alert includes information regarding the determined orientation and the quantitative acceleration.

6. The method of claim 1, wherein determining the quantitative acceleration of the anesthetic vaporizer based on the acceleration vectors measured by the accelerometer coupled within the anesthetic vaporizer is responsive to the anesthetic vaporizer being powered on, and wherein the sensor is a level sensor that monitors the level of an anesthetic agent within the anesthetic vaporizer.

7. The method of claim 6, wherein the acceleration vectors measured by the accelerometer coupled within the anesthetic vaporizer are measured while the anesthetic vaporizer is unpowered, and wherein the alert includes one or both of an audible alert and a visual alert.

8. The method of claim 1, further comprising disabling usage of the anesthetic vaporizer in response to the quantitative acceleration exceeding the acceleration threshold and communicating the alert to an inventory management system.

9. The method of claim 1, further comprising communicating the alert and a magnitude of each of the acceleration vectors to an inventory management system via a wireless communication protocol in response to the quantitative acceleration exceeding the acceleration threshold.

10. The method of claim 1, further comprising:
determining a tilt of the anesthetic vaporizer during usage based on measurements received in real-time from the accelerometer coupled within the anesthetic vaporizer; and
outputting a tilt alert in response to the tilt of the anesthetic vaporizer exceeding a threshold tilt.

11. A system for an anesthetic vaporizer, comprising:
an accelerometer positioned within an external housing of the anesthetic vaporizer;
a touch sensor positioned on the external housing of the anesthetic vaporizer;
a sensor, wherein the sensor is an ultrasonic leak detector coupled to the anesthetic vaporizer;
a gyroscope coupled to the anesthetic vaporizer;
a first power source that provides continuous electrical power to the accelerometer; and
a second power source that provides electrical power to a controller while the anesthetic vaporizer is powered on and not while the anesthetic vaporizer is powered off, the controller storing executable instructions in non-transitory memory that, when executed, cause the controller to:
receive measurements from the accelerometer recorded while the anesthetic vaporizer is powered off;
resolve a quantitative acceleration from the received measurements;
determine an orientation of the anesthetic vaporizer from the received measurements;

select an acceleration threshold from a plurality of different acceleration thresholds stored in the non-transitory memory based on the determined orientation;

activate the ultrasonic leak detector in response to the quantitative acceleration exceeding the acceleration threshold to detect leakage of pressurized air from the anesthetic vaporizer; and output a first type of alert in response to the quantitative acceleration exceeding the acceleration threshold.

12. The system of claim 11, wherein the touch sensor is configured to detect if and where the anesthetic vaporizer was being held prior to the quantitative acceleration exceeding the acceleration threshold.

13. The system of claim 11, wherein the controller includes further instructions stored in the non-transitory memory that, when executed, cause the controller to:

receive real-time measurements from the accelerometer while the anesthetic vaporizer is powered on;

determine a real-time tilt of the anesthetic vaporizer based on the real-time measurements received from the accelerometer; and output a second type of alert in response to the real-time tilt exceeding a tilt threshold.

14. A method for detecting a fall of an anesthetic vaporizer, comprising:

upon start-up of the anesthetic vaporizer, receiving, at a controller, acceleration measurements recorded by an accelerometer coupled within the anesthetic vaporizer while the anesthetic vaporizer is powered off, wherein the accelerometer is powered by a first power source that provides continuous electrical power, and wherein the controller is powered by a second power source the provides power while the anesthetic vaporizer is powered on and not while the anesthetic vaporizer is powered off;

determining a magnitude and direction of an acceleration vector from the acceleration measurements;

selecting an acceleration threshold based on the direction of the acceleration vector;

activating a level sensor responsive to the quantitative acceleration exceeding the acceleration threshold, wherein the level sensor is coupled to a vaporizing chamber of the anesthetic vaporizer, and wherein the level sensor monitors the level of an anesthetic agent in the anesthetic vaporizer; and outputting a drop alert in response to the magnitude of the acceleration vector exceeding the acceleration threshold.

15. The method of claim 14, wherein selecting the acceleration threshold based on the direction of the acceleration vector comprises inputting the direction of the acceleration vector into an array storing a plurality of acceleration thresholds, each of the plurality of acceleration thresholds corresponding to a different direction of the acceleration vector.

16. The method of claim 14, wherein the drop alert comprises an audible alarm.

17. The method of claim 14, further comprising:

disabling the anesthetic vaporizer in response to the magnitude of the acceleration vector exceeding the acceleration threshold; and not disabling the anesthetic vaporizer in response to the magnitude of the acceleration vector not exceeding the acceleration threshold.

18. The method of claim 14, further comprising outputting an inspection checklist in response to the magnitude of the acceleration vector exceeding the acceleration threshold.

19. The method of claim 18, wherein the inspection checklist is selected from a plurality of different inspection checklists based on the direction of the acceleration vector, and wherein both of the drop alert and the inspection checklist are communicated to an inventory management system via wireless communication.

\* \* \* \* \*